Figure 1:
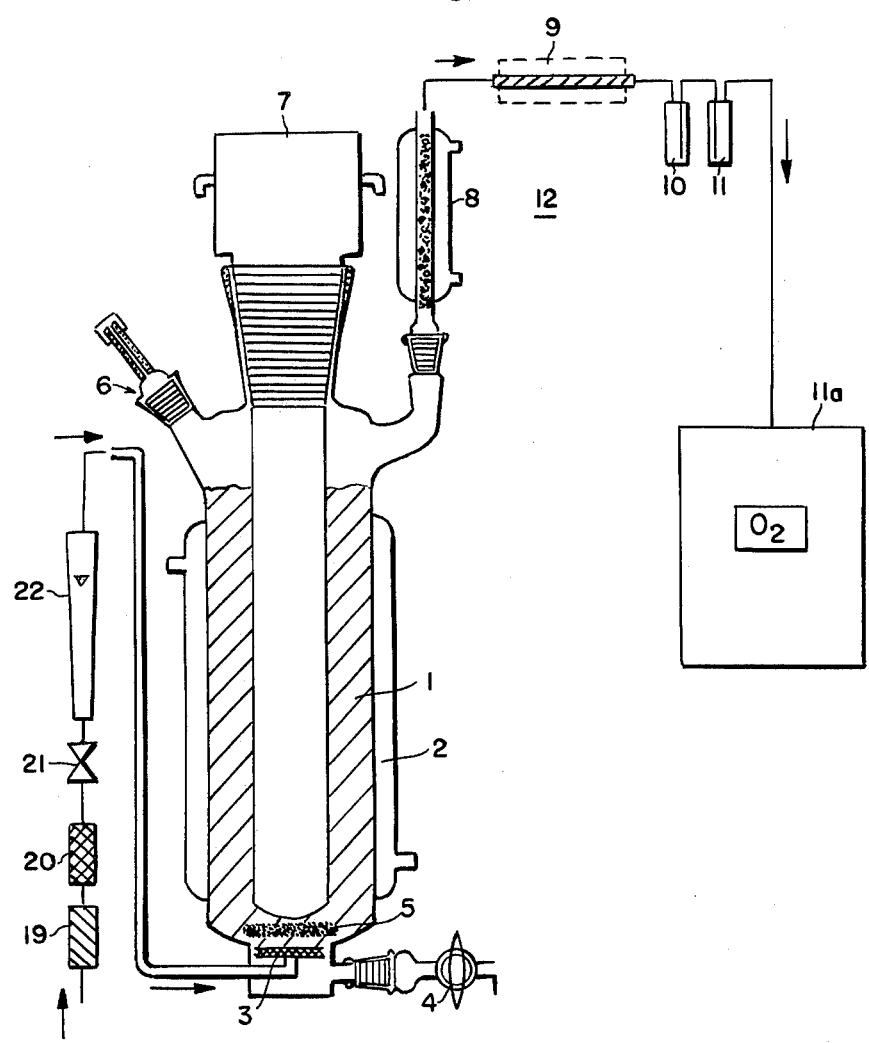

United States Patent [19]

Wölfel

[11] 4,244,696
[45] Jan. 13, 1981

[54] METHOD AND APPARATUS FOR DETERMINING THE CHEMICAL OXYGEN DEMAND OF ORGANIC MATERIALS DISSOLVED IN WATER

[75] Inventor: Peter Wölfel, Langenau, Fed. Rep. of Germany

[73] Assignee: Deutscher Verein des Gas- und Wasserfachs e.V., "DVGW-Forschungsstelle", Fed. Rep. of Germany

[21] Appl. No.: 932,673

[22] Filed: Aug. 10, 1978

[51] Int. Cl.³ .............................................. G01N 33/18
[52] U.S. Cl. .................... 23/230 R; 23/906; 422/79
[58] Field of Search ................. 422/79, 24; 23/230 R, 23/906; 210/63 R; 250/432

[56] References Cited

U.S. PATENT DOCUMENTS

| 2,040,264 | 5/1936 | Mancini et al. ...................... 250/432 |
| 3,510,407 | 5/1970 | Stack, Jr. ......................... 23/230 R X |
| 3,540,849 | 11/1970 | Neti et al. ............................ 23/230 R |
| 3,558,277 | 1/1971 | Laman et al. ....................... 23/230 R |
| 3,679,364 | 7/1972 | Teal et al. .......................... 23/230 PC |
| 3,810,738 | 5/1974 | Fleischmann ...................... 422/79 X |
| 3,819,516 | 6/1974 | Murchison et al. ............... 210/63 R |
| 3,945,799 | 3/1976 | Honma ............................ 23/230 PC |

FOREIGN PATENT DOCUMENTS 45-15677  6/1970  Japan ..................... 23/230 R

Primary Examiner—Arnold Turk
Attorney, Agent, or Firm—Richard L. Johnston

[57] ABSTRACT

Method and an apparatus for determining the chemical oxygen demand (COD) of waters by a photochemically accelerated oxidation with oxygen. This method, if desired, may be combined with the step of measuring the contents which the waters have in organically bound carbon.

7 Claims, 3 Drawing Figures

METHOD AND APPARATUS FOR DETERMINING THE CHEMICAL OXYGEN DEMAND OF ORGANIC MATERIALS DISSOLVED IN WATER

This invention concerns a method and an apparatus for determining the chemical oxygen demand (COD) of waters by a photochemically accelerated oxidation with oxygen, this method being combined, if desired, with the step of measuring the contents in the waters of organically bound carbon.

It has herebefore been the common practice in determining the chemical oxygen demand to oxidize the organic materials contained in the sample of waste water with chromosulfuric acid. With this method, the chemical oxygen demand is determined by measuring the hexavalent chromium used up in the oxidation of the organic materials by titration. The use of hot chromosulfuric acid in this method however calls for precautionary measures to be taken. Moreover, many difficulties will arise as a result of the toxicity of the chromiferous sulfuric acid obtained. Added to this must be the fact that the chromosulfuric acid is given in general an addition of $Ag_2SO_4$ to improve its oxidizing action and of highly toxic $HgSO_4$ to eliminate the obnoxious effect of the chlorides so that about 350 ml of dilute sulfuric acid are obtained in each analysis containing about 20 mg of $Cr^{3+}$ and $Cr^{6+}$, about 300 mg of $Ag^+$ and about 700 mg of $Hg^{2+}$. As a result, when achieving the analyses by this method, the waste waters will have to be subjected to an additional treatment.

To remedy these shortcomings, which are known to plague an automatic operation in the practice of the analyses, methods and apparatus have been developed in which the water is vaporized and the organic materials are burnt. These methods, however, though useful in measuring the amount of spent oxygen or of carbon monoxide, if carbondioxide is the oxidant, are seriously plagued by the fact that the inorganic nitrogen compounds ($NH_4^+$ and $NO_3^-$) too, as are contained in any water, are oxidized or, if carbon dioxide is employed, are reduced. Thus, an analysis by either of these techniques is not limited, as opposed to the purpose for which it is carried out, to the determination of the oxygen required for the oxidation of the organic materials contained in the water and, as a result, calls for an additional measurement of the $NH_4^+$ and $NO_3^-$ concentrations and a subsequent recalculation. In this latter case, however, difficulties will arise owing to the fact that the reaction does not constantly take an even course.

The object of this invention resides in the provision of a method and an apparatus by which the chemical oxygen demand of organic materials dissolved in water can be determined without having to resort to toxic reagents and without the inorganic nitrogen compounds being converted to any appreciable extent.

This object of the invention will be accomplished by a process and an apparatus with which the oxidation of the materials dissolved in water is effectuated with oxygen under the action of the UV radiation of a mercury vapor lamp.

In view of these objects, the invention concerns a method for determining the chemical oxygen demand of organic materials dissolved in water by oxidation, wherein a sample of water is subjected to a photochemical oxidation under the action of the UV radiation of a mercury vapor lamp, in the presence of an inert carrier gas which contains less than 5 percent by volume of oxygen and wherein the chemical oxygen demand of the organic materials dissolved in the water sample is determined by measuring the amount of spent oxygen in the carrier gas, if desired after the removal of the carbon dioxide formed by the oxidation.

It is surprising that the oxygen which the carrier gas contains in a low concentration should effectuate so rapid and complete an oxidation of the dissolved organic materials that this reaction can be made the basis of an analytic method.

The temperature in the vessel in which the radiation is achieved is generally kept at from 30° to 50° C., preferably at about 40° C. The sample of water may vary in quantity depending on its contents of organic materials and the size of the apparatus used for the analysis. Typically, a sample of 1 ml containing up to 10 mg of carbon per one liter will do. The preferred inert carrier gas is nitrogen, but other inert gases, such as noble gases, may also be used. The pressure at which the inert gas is used is not an essential factor of the invention. The analysis may be operated at normal as well as at moderately reduced or moderately increased pressure, i.e. at about 0.5 bar. Again, the quantity of gas required depends on the size of the apparatus, the size of the sample and the carbon contents of the latter. In common practice, the quantity of carrier gas required is from about 20 to 60 l/h.

In a preferred embodiment of the invention the inert carrier gas used in the process contains less than 3 percent by volume, more specifically less than 1 percent by volume, of oxygen. There is no defined bottom limit for the oxygen contents of the carrier gas in the invention, because even extremely slight amounts and even traces of oxygen in the carrier gas still have a function in the process. Thus, highly satisfactory results still will be obtained when the carrier gas used, for example nitrogen, contains less than 0.1 percent by volume, more specifically of from 0.005 to 0.01 percent by volume, of oxygen.

Various methods may be used for measuring the residual oxygen in the carrier gas after the photochemical oxidation. Any device commonly used for measuring the oxygen contents in gas mixtures will serve the purpose. A preferred embodiment, however, comprises reacting the residual oxygen with suitable reactants, after removing the carbon dioxide formed in the oxidation, measuring the residual amount of oxygen contained in the reaction products thus formed and determining the consumption of oxygen by the data obtained for the residual amount of oxygen.

A specially preferred method for measuring the amount of residual oxygen in spent carrier gas consists in stripping the carrier gas of carbon dioxide subsequent to the oxidation, for example by binding it to an alkaline agent, such as caustic alkali, and passing the carrier gas over red hot graphite or live coal. If this be done, the oxygen reacts to form carbon monoxide which may directly be analyzed by conventional means. Alternatively, the carbon monoxide may be oxidized to form carbon dioxide and this again, which may also be referred to as secondary carbon dioxide, may be measured with any conventional analyzer.

Further objects and advantages are within the scope of this invention and will be apparent from the specification hereinafter when read with reference to the accompanying drawings.

The characteristic elements of the apparatus used in the practice of the process according to the invention are a UV radiation vessel for the photochemical oxidation of organic materials dissolved in water, a mercury vapor lamp, means for feeding in the sample of water, means for feeding in a carrier gas containing oxygen and means for measuring the residual oxygen in the spent carrier gas.

The radiation vessel, the means for introducing the sample of water and the means for the feed of the carrier gas may be those described in the German laid-open patent application DE-OS No. 2,362,773 in connection with an apparatus for measuring organically bound carbon in water by photochemical oxidation, but other means adapted to serve the purpose of this invention may be used as well. Thus, for example, a tubular radiation vessel having a UV lamp annularly mounted on its outside may be used instead of a cup-like radiation vessel having a rod-shaped UV lamp arranged inside it. In this case, the sample of water may be flown as a thin film over the inner wall of the quartz tube and exposed to the action of the outside radiator for oxidation. An apparatus of this type may be used with special advantage for a continuous determination of the oxygen demand of organic materials dissolved in water.

Various modifications are possible in that part of the apparatus in which the residual oxygen of the carrier gas is measured after the oxidation. The type of any such change in the apparatus depends on whether the residual oxygen is to be measured as such or as a conversion product.

Figure 2:
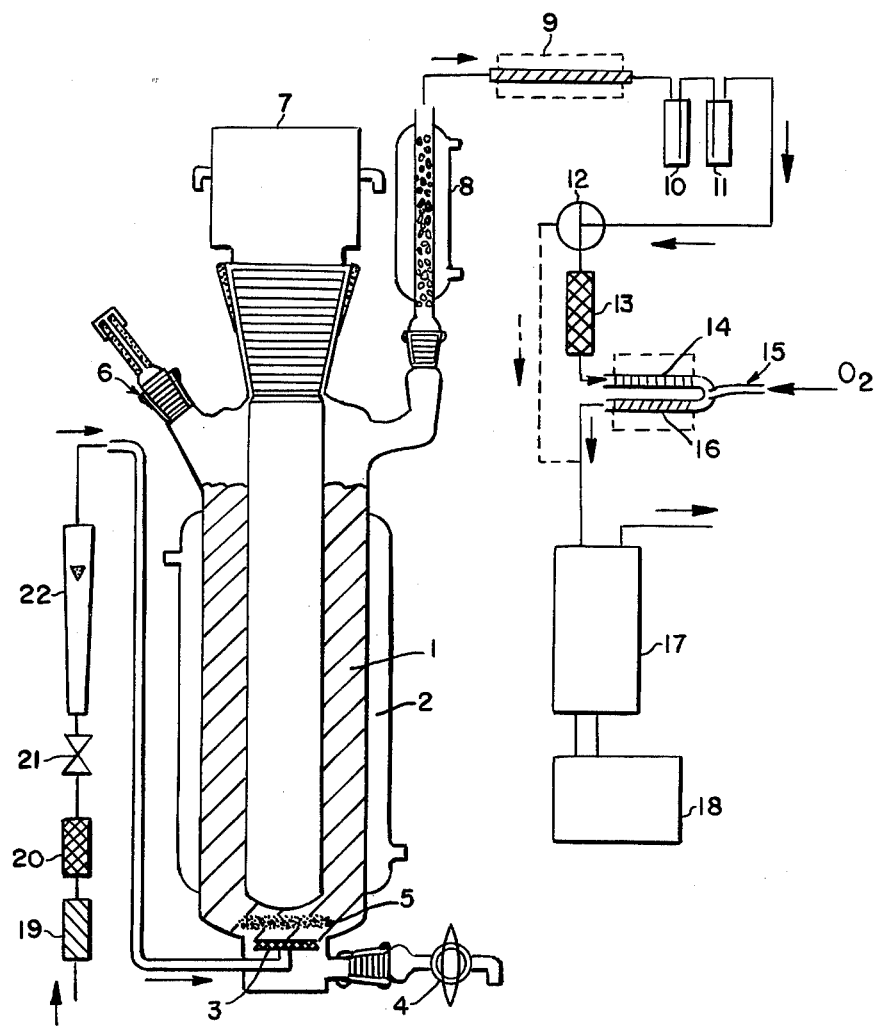
Figure 3:
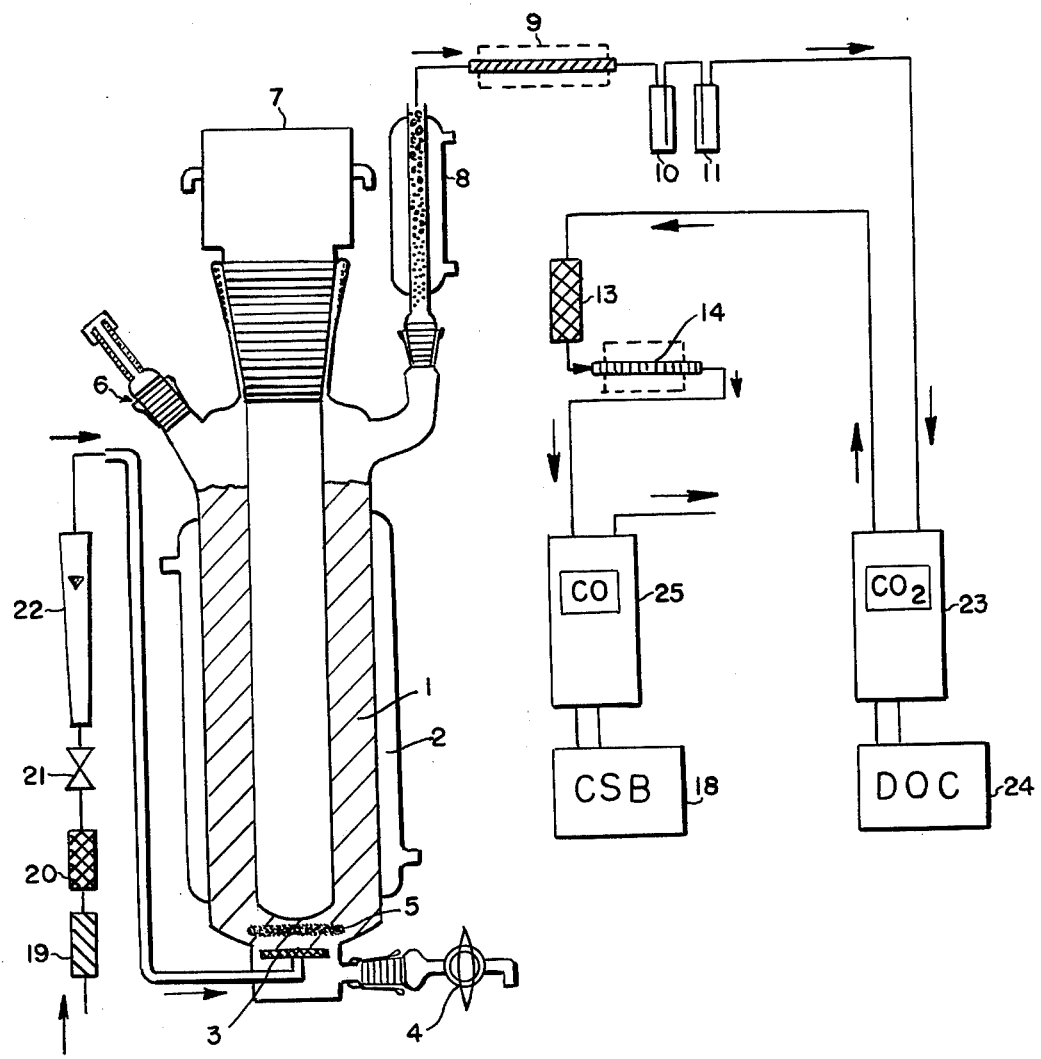

The invention will hereinafter be described in greater detail with reference to the accompanying drawing in which FIG. 1 depicts an apparatus for determining the chemical oxygen demand by the direct measurement of the residual oxygen in the carrier gas;

FIG. 2 depicts an apparatus for determing the chemical oxygen demand by measuring the residual oxygen in the carrier gas after its conversion into carbon dioxide, and FIG. 3 depicts an apparatus for determining the chemical oxygen demand by measuring the residual oxygen in the carrier gas after its conversion into carbon monoxide.

The apparatus shown in FIGS. 2 and 3 are also adapted for use in measuring organically combined carbon.

The apparatus depicted in FIGS. 1, 2 and 3 are equal in their parts for the introduction of the water sample, for the feed of the carrier gas and for the photochemical oxidation, but differ in their means for the measurement of the residual oxygen contained in the carrier gas.

All of these apparatus have a radiation vessel 1 and a cooling jacket 2 for the radiation vessel. The cooling jacket 2, as that of a mercury vapor lamp 7 substantially arranged in a central position in the vessel 1, has water flowing through it as a coolant. The water is maintained at a temperature of between 30° and 50° C., preferably of about 40° C., by a thermostat. From the radiation vessel 1, in which the level of the water rises as samples of water are fed in, water is intermittently discharged through cock 4.

The gas mixture of nitrogen and oxygen, which enters the vessel through the sintered glass bottom 3 is continuously flown through the water contained in the reaction vessel, the water being adjusted to a pH of less than 4.5, more preferably to a pH of 2 or less, by means of concentrated phosphoric or concentrated sulfuric acid. The water in the radiation vessel 1 is intensely agitated by a magnetic bar 5 which rotates at high speed above the sintered glass bottom 3. Prior to this step, the gas stream is stripped of moisture and carbon dioxide in dryers charged with silica gel 19 and sodium asbestos 20 and adjusted to a constant speed of flow by means of a needle valve 21 and a speedometer 22. The gas is either nitrogen which has not been completely stripped of oxygen or nitrogen to which a well defined portion of oxygen has been added prior to drying.

After leaving the water in the reactor, the gas stream passes through the cooler 8 into the tubular furnace 9. The cooler 8 is preferably filled with glass spirals, Raschig rings or similar materials and functions to condense the moisture which adheres to the gas stream. In a preferred embodiment, the cooler is so arranged that the condensate flows back into the apparatus as formed. The tubular furnace 9 includes a quartz tube filled with quartz pieces which are coated with platinum as a catalyst. The platinum catalyst functions to destroy the ozone formed by the radiation of the oxygen.

After having passed the tubular furnace 9, the gas stream flows through a safety washing bottle 10 into the washing bottle 11 which is filled with sulfuric acid. Here the gas is stripped of any residual moisture left and, as a result, is ready for use for the measurement of residual oxygen by any of the direct or indirect methods. In the apparatus shown in FIG. 1 the gas is immediately supplied to a device 11a for measuring the oxygen in gas mixtures. In the apparatus shown in FIG. 2 the gas is flown through a tube 13 charged with sodium asbestos, in which the carbon dioxide formed in the oxidation of the organic materials is removed. The gas stream is subsequently passed through a red hot quartz tube of about 12 mm in diameter, which is filled with graphite or coal over a length of about 180 to 220 mm. In this tube the oxygen reacts to form carbon monoxide. The carbon monoxide is further oxidized to form carbon dioxide in a second red hot quartz tube 16 which is filled with quartz pieces coated with platinum as a catalyst. From tube 16 the carbon dioxide passes into the $CO_2$ gas analyzer 17. The oxygen needed to oxidize the carbon monoxide into carbon dioxide is metered in at 15 between the tubes 14 and 16.

In the practice of the analysis a sample of water is injected by means of a syringe through the opening 6, the UV lamp being deenergized. The sample immediately flows into the highly acid and carbon-free water of the radiation apparatus, where it is stripped of dissolved portions of oxygen and inorganic carbon dioxide by the carrier gas stream. This process step is complete, when the recorder of the potentiometer-type recorder 18 connected to the $CO_2$ gas analyzer 17 reads out a constant level in the $CO_2$ concentration. Now the UV lamp is energized. By the action of its rays is in the presence of oxygen, the total amount of the organic compounds dissolved are oxidized. The oxygen needed is taken from the carrier gas stream and read out on the recorder in terms of the decrease in the amount of the carbon dioxide secondarily formed from the residual oxygen. When the recorder has returned to the base line, the total of the organic materials has undergone oxidation and there is no further consumption of oxygen out of the carrier gas. The UV lamp can then be deenergized again. In the ordinary case, it takes about 5 to 10 minutes to determine the chemical oxygen demand by the method and apparatus according to the invention.

During the oxidation the $CO_2$ gas analyzer continuously analyzes the concentration of oxygen in the carrier gas, at any given time, by way of the carbon dioxide formed therefrom, so that a curve appears on the recorder whose area is directly proportional to the amount of oxygen needed for the oxidation of the samples. On a recorder fitted with an integrating element this area beneath the curve is reflected in scale divisions. In combination with a calibration, which may be accomplished, for example, by the oxidation of a solution of oxalic acid whose oxygen demand is known, the chemical oxygen demand of the unknown sample can be determined.

In the practice of the invention a low pressure mercury vapor lamp emitting rays of a wave length of $\Lambda_1 = 254$ nm and $\Lambda_2 = 185$ nm has performed satisfactorily as a radiation source. With a UV lamp of this type the photochemical oxidation will proceed completely at a rapid course.

The particular benefits included in the method and apparatus according to the invention reside in the fact that only one apparatus is required for determining the chemical oxygen demand and for measuring the organically combined carbon. As is apparent from FIG. 2 of the drawing, the apparatus shown may be alternatively used to determine the chemical oxygen demand or to measure the organically combined carbon dissolved, depending upon whether the gas stream is passed, by means of the threeway cock 12, through the $CO_2$ adsorbing agent 13 and the red hot quartz tubes 14 and 16, charged with graphite and a platinum catalyst, respectively, or whether the gas stream, after having left the washing bottle 11 filled with sulfuric acid, is immediately passed into the $CO_2$ gas analyzer. Since by proceeding in the manner described each sample has to be fed in twice, once for the determination of the chemical oxygen demand and a second time for the measurement of the organically combined carbon, special advantages are achieved by using the apparatus depicted in FIG. 3 of the drawing. With this apparatus one single sample is required for determining the chemical oxygen demand and measuring the contents of organically combined carbon thereof. The difference between the apparatus according to FIG. 2 and that according to FIG. 3 mainly resides in the fact that in the latter case the carbon dioxide formed by the oxidation of the organic materials is recorded in a $CO_2$ analyzer prior to being removed from the carrier gas stream in the $CO_2$ adsorption tower 13. By another characteristic feature of the apparatus according to FIG. 3, the oxygen in the carrier gas needs be reacted only to form carbon monoxide so that tube 16 with its charge of platinum catalyst and the metering in of oxygen at point 15 are no longer necessary. In this case, the oxygen concentration in the carrier gas is no longer ascertained by measuring the $CO_2$ contents, but by measuring the CO contents of the gas in an appropriate gas analyzer for carbon monoxide. It is understood, however, that here again the oxygen may be reacted to form $CO_2$ and that the latter may be used to measure the amount of the oxygen spent.

In the apparatus according to FIG. 3 two measuring elements are required to determine the chemical oxygen demand and to measure the amount of organically combined carbon with one and the same sample. To avoid the necessity of having to use such measuring elements, the apparatus according to FIG. 2 may be changed to the effect that, instead of being removed by way of the sodium-asbestos-filled tube, the $CO_2$ may be removed by way of an adsorption agent which is capable of regeneration and may also be placed in a tube. In this case, the procedure comprises the steps of determining the chemical oxygen demand first, expelling the $CO_2$ from the adsorption agent by heating and directly feeding it into the gas analyzer for measurement. This allows to determine in conventional manner the amount of carbon organically combined in the sample.

It will be apparent from the foregoing description that the method and apparatus of the invention provide a high-precision and rapid mode of determining the chemical oxygen demand in water, while avoiding the shortcomings inherent in the chemical wet oxidation with chromosulfuric acid herebefore referred to. When using a commercial $CO_2$ gas analyzer having a measuring range of from 0 to 100 ppm of carbon dioxide, the lower detection limit lies by about two powers of ten below the detection limit attainable by the conventional chromosulfuric acid method. The fact that the invention is practiced in the absence of high temperatures and dangerous chemicals is coupled with the benefit that the apparatus are easy to operate with little need for repairs. Special emphasis be given to the important fact that one sample of water only is needed for determining the chemical oxygen demand and measuring the amount of organically combined carbon. For further details concerning the measurement of the amount of organically combined carbon German laid-open patent application DE-OS No. 2,362,773 should be referred to.

What is claimed is:

1. A method for determining the chemical oxygen demand of organic materials dissolved in water by oxidation which comprises subjecting a sample of water to a photochemical oxidation under the action of the UV radiation of a mercury vapor lamp, in the presence of an inert carrier gas which contains less than 5 percent by volume of oxygen, and determining the chemical oxygen demand of the organic materials dissolved in the water by measuring the amount of spent oxygen in the carrier gas.

2. A method as in claim 1 which comprises measuring the amount of spent oxygen in the carrier gas after removing the carbon dioxide formed by the oxidation.

3. A method as in claim 1 which comprises using an inert carrier gas containing less than 3 percent by volume of oxygen.

4. A method as in claim 1 which comprises using an inert carrier gas containing less than 1 percent by volume of oxygen.

5. A method as in claim 1 which comprises determining the amount of spent oxygen in the carrier gas by measuring the residual amount of oxygen in the carrier gas.

6. A method as in claim 1 which comprises determining the amount of spent oxygen by reacting the residual oxygen of the carrier gas to form carbon monoxide and measuring the amount of carbon monoxide.

7. A method as in claim 2 which comprises determining the amount of spent oxygen by subsequent to removing the carbon dioxide formed in the oxidation, reacting the residual oxygen of the carrier gas to form carbon monoxide first and then to form carbon dioxide and measuring the amount of carbon dioxide.

* * * * *